United States Patent
Souzy et al.

(10) Patent No.: US 8,790,622 B2
(45) Date of Patent: Jul. 29, 2014

(54) COSMETIC FORMULATION CONTAINING A NON WATER-SOLUBLE AMPHIPHILIC COPOLYMER AS THICKENING AGENT

(75) Inventors: Renaud Souzy, Caluire et Cuire (FR); Jean-Marc Suau, Lucenay (FR); Yves Kensicher, Theize (FR); Olivier Guerret, Pern (FR)

(73) Assignee: Coatex, Genay (FR)

( * ) Notice: Subject to any disclaimer, the term of this patent is extended or adjusted under 35 U.S.C. 154(b) by 0 days.

(21) Appl. No.: 13/413,719

(22) Filed: Mar. 7, 2012

(65) Prior Publication Data
US 2012/0230920 A1 Sep. 13, 2012

Related U.S. Application Data

(60) Provisional application No. 61/452,725, filed on Mar. 15, 2011.

(30) Foreign Application Priority Data

Mar. 7, 2011 (FR) .................................... 11 51811

(51) Int. Cl.
| | | |
|---|---|---|
| A61K 8/00 | (2006.01) | |
| A61K 9/00 | (2006.01) | |
| A61K 47/32 | (2006.01) | |
| C08L 71/02 | (2006.01) | |
| A61Q 19/00 | (2006.01) | |
| A61K 8/86 | (2006.01) | |

(52) U.S. Cl.
CPC . *A61K 8/86* (2013.01); *C08L 71/02* (2013.01); *A61K 2800/48* (2013.01); *A61Q 19/00* (2013.01); *A61K 2800/548* (2013.01)
USPC ........................................ 424/47; 514/772.3

(58) Field of Classification Search
None
See application file for complete search history.

(56) References Cited

U.S. PATENT DOCUMENTS

| | | | |
|---|---|---|---|
| 6,262,152 B1 * | 7/2001 | Fryd et al. ..................... 524/90 |
| 2003/0129151 A1 * | 7/2003 | Candau et al. .................. 424/59 |
| 2003/0207988 A1 | 11/2003 | Tamareselvy et al. |
| 2008/0045646 A1 | 2/2008 | Tamareselvy et al. |
| 2009/0208441 A1 | 8/2009 | Couturier et al. |
| 2010/0178257 A1 | 7/2010 | Farcet |

FOREIGN PATENT DOCUMENTS

| | | | | |
|---|---|---|---|---|
| EP | 1 160 265 | * | 12/2001 | ............ C08F 220/04 |
| EP | 1 160 265 A1 | | 12/2001 | |
| EP | 2 147 940 A1 | | 1/2010 | |
| FR | 2 898 127 | | 9/2007 | |
| WO | WO 03/062288 A1 | | 7/2003 | |

OTHER PUBLICATIONS

U.S. Appl. No. 13/456,438, filed Apr. 26, 2012, Suau, et al.
Preliminary Search Report issued Nov. 9, 2011 in French Application No. 1151811 (With English Translation of Category of Cited Documents).
"Acrylates/Methoxy PEG-15 Methacrylate Copolymer", Internet Citation, URL [http://www.specialchem4cosmetics.com/services/inci/ingredient.aspx?], Jan. 1, 2011, XP007919689, 1 page.
U.S. Appl. No. 13/415,001, filed Mar. 8, 2012, Suau, et al.
U.S. Appl. No. 14/147,702, filed Jan. 6, 2014, Suau, et al.

* cited by examiner

*Primary Examiner* — Carlos Azpuru
*Assistant Examiner* — David Browe
(74) *Attorney, Agent, or Firm* — Oblon, Spivak, McClelland, Maier & Neustadt, L.L.P.

(57) ABSTRACT

The present invention concerns formulations containing one or more comb structure amphiphilic copolymers that are both rich in hydrophobic monomers and in polyalkylene glycol monomers. Cosmetic formulations. Methods of thickening.

11 Claims, No Drawings

COSMETIC FORMULATION CONTAINING A NON WATER-SOLUBLE AMPHIPHILIC COPOLYMER AS THICKENING AGENT

REFERENCE TO PRIOR APPLICATIONS

This application claims priority to U.S. provisional application Ser. No. 61/452,725, filed Mar. 15, 2011; and to French patent application 11 51811, filed Mar. 7, 2011, both incorporated herein by reference.

FIELD OF THE INVENTION

The present invention concerns formulations including preferably cosmetic formulations containing as a thickening agent one or more comb structure amphiphilic copolymers that are both rich in hydrophobic monomers and in polyalkylene glycol monomers. They present in the form of solid particle dispersions in water, the mean molar mass by weight of which is in the order of millions of grams per mole. Once they are transformed into salts, they acquire a water-soluble character and allow the efficient thickening of a cosmetic formulation containing them, particularly for a pH between 5 and 7. This makes them particularly suitable for cosmetic formulations for skin application, such as notably make-up and body care products.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. In this regard, the description herein is to be understood as illustrative in nature, and not as restrictive.

BACKGROUND OF THE INVENTION

A number of cosmetic formulations consist mostly of water and a non-aqueous phase, in particular with a base of oils, waxes, surfactants, solvents or other excipients. These include creams, foaming agents, makeup products, etc. that may be designated by the expression cosmetic formulations for skin application, in the sense that they are intended to be applied to the skin. Quite naturally, an attempt is made to thicken such formulations in the pH range corresponding to that of the skin, i.e. values between 5 and 7, and preferentially between 5 and 6.5, very preferentially between 5.5 and 6.

There are a certain number of technical solutions to this problem which can be classified into 4 categories: the implementation of polymers of high molecular weight and in the powder form, the so-called "back acid" technique based on acrylic polymers in direct emulsion of polymer particles in water, the implementation of other polymers always in the form of direct emulsions, and finally the use of water-in-oil emulsions.

In the first category, reference can be made to document EP 1 138 703 A1 which describes a topical cosmetic composition including a high molecular weight polymer based on at least one monomer possessing a strong free acid function copolymerized with at least one esterified monomer and terminated by a hydrophobic group with 8 to 30 carbon atoms. The above-noted polymer is an emulsifying polymer in the solid form; it can be dispersed in water, and it enables the thickening of the composition that contains it, notably for pH values in the neighbourhood of 5.

However, these polymers have the disadvantages of the use of a powder: difficulties with transportation and cleaning, dangerousness of the product in relation to its powdery, irritating and particulate character. In addition, these polymers must be made soluble in the medium to be thickened by the introduction of surfactants. These surfactants are additional formulation additives that make the formulation more complex and can interact with surfactants already contained in the said formulation, sometimes creating adverse effects (including phase separation, formation of residual insolubles).

Also known is the so-called "back-acid" technique, as described in document WO 01/76 552. This is a process consisting of introducing a surfactant and an inflatable acrylic alkali copolymer into an aqueous medium. The latter leads to a thickening effect when its carboxylic acid groups are neutralized: There is then the creation of a three-dimensional network which leads to an increase in the viscosity of the aqueous phase. Such an effect can be triggered in a pH range in the neighbourhood of 6, the role of the surfactant being to maintain the thickening effect even when the pH is decreased.

To the above-noted mechanism can be added an associative mechanism based on the presence of a hydrophobic monomer: This is what is described by document WO 03/62 288 which also aims at thickening acidic pH formulations. The same is true for document U.S. Pat. No. 4,529,773 A1. As with the back-acid method, the presence of a surfactant in the form of an additional product is therefore necessary, resulting in the disadvantages already mentioned.

Also known are a certain number of documents that describe the implementation of other polymers in emulsion. As such, document EP 0 824 914 B1 describes a polymer containing a cationic amino monomer. The desired thickening effect will be obtained at an acidic pH via the ionization of the cationic amino monomer. In document WO 2004/024 779, the cationicity of the proposed polymer is provided by an amino-substituted vinyl monomer. Thickening an acidic pH aqueous medium is also achieved here. However, the toxicity of cationic polymers to aquatic wildlife is well known: now they are unfortunately found at the end of the life cycle in our rivers and tributaries into which they are discharged via the domestic wastewater system.

Finally, water-in-oil emulsions and their applications as thickening agents are known in the field of cosmetics, as disclosed in documents WO 2004 063228 A1 and GB 2 422 605 A1. Nevertheless, these structures require the presence of surfactants and solvents to ensure their stability, and the disadvantages mentioned above are then encountered.

SUMMARY OF THE INVENTION

The inventors, in continuing their research aimed at thickening aqueous compositions, particularly at pH levels below 7, while lessening the impact of the disadvantages of the methods of the prior art, have developed a thickening process using non water-soluble copolymers with a comb structure having a (meth)acrylic skeleton on which are grafted side chains containing at least one hydrophobic monomer of the styrene type or its derivatives or (meth)acrylic ester on C1 to C4, and at least one hydroxy or methoxy polylakylene glycol monomer.

The levels of comonomers are such that these copolymers are amphiphilic: they are both rich in hydrophobic monomers and in monomer polyalkylene glycols in polymerized form.

They present in the form of solid particle dispersions in water, with their mean molar mass by weight being 1,000,000-15,000,000 g/mol. Once they are transformed into salts, these polymers increase their solubility in water. They were mentioned for the first time in French Patent Applications filed under the numbers FR 10 56658 and FR 10 56659, both incorporated herein by reference. These structures can be obtained by conventional polymerization processes using known initiators (see for example documents EP 1 981 920 A1 and EP 0 819 704 A1 both incorporated herein by reference).

These copolymers allow the effective thickening of an aqueous formulation at a pH less than 7, including a cosmetic formulation containing an aqueous phase and a non-aqueous phase intended for a cutaneous application.

DETAILED DESCRIPTION OF THE PREFERRED EMBODIMENTS

In addition to what has been described above, an object of the present invention is a formulation, preferably a cosmetic formulation, comprising an aqueous phase and a non-aqueous phase and characterized in that it comprises at least one amphiphilic non-water-soluble comb copolymer comprising, consisting essentially of, or consisting of, expressed in % by weight of each of the comonomers:
- a) from 30% to 60% of at least one hydroxy and/or methoxy polyalkylene glycol monomer with the formula $R\text{-}(EO)_m\text{-}(PO)_n\text{-}R'$, with:
  - m and n designating integers that are less than or equal to 150, with at least one of them being non-zero,
  - EO and PO respectively designating ethylene oxide and propylene oxide,
  - R designating the methacrylate or methacrylurethane function,
  - R' designating a hydroxy or methoxy group,
- b) from 20% to 60% of at least one hydrophobic monomer chosen from styrene, paratertiobutylstyrene, and (meth) acrylic esters with 1 to 4 carbon atoms on the ester group,
- c) from 0.1% to 10% of at least one monomer which is acrylic and/or methacrylic acid,
- d) from 0 to 15% of an associative monomer with the formula $R\text{-}(EO)_m\text{-}(PO)_n\text{-}R'$, with:
  - m and n designating integers that are less than or equal to 150, with at least one of them being non-zero,
  - EO and PO respectively designating ethylene oxide and propylene oxide,
  - R designating a polymerizable function, preferentially the methacrylate or methacrylurethane function,
  - R' designating an alkyl or aryl or alkylaryl group with 8 to 36 carbon atoms, linear or branched,
- e) from 0 to 5% of a monomer with at least two ethylenic unsaturations,
the sum of the percentages a), b), c), d) and e) being equal to 100%.

Of course, and as is well known to those of skill in this art, in the present copolymers the comonomers are present in polymerized form but are discussed as comonomers.

The inventive formulation is also preferably characterized in that the copolymer presents a mean molar mass by weight of between 1,000,000 and 15,000,000 g/mol, preferentially between 1,000,000 and 6,000,000 g/mol as determined by GPC. Reference will be made to the measurement technique described in document WO 07/069,037 A1.

The inventive copolymers can be obtained by known methods of conventional free radical copolymerization in solution, in direct or inverse emulsion, in suspension or precipitation in suitable solvents, in the presence of known starters and transfer agents, or again, by processes of controlled radical polymerization such as the method known as Reversible Addition Fragmentation Transfer (RAFT), the method known as Atom Transfer Radical Polymerization (ATRP), the method known as Nitroxide Mediated Polymerization (NMP), or again, the method referred to as Cobaloxime Mediated Free Radical Polymerization.

It is preferably obtained in the acid and possibly distilled form. It can also be partially or totally neutralized by one or more neutralization agents preferentially selected from the hydroxides of sodium and potassium and their mixtures.

The invention formulation is also preferably characterized in that it includes from:
- a) 10 to 99.9%, preferably 15 to 99.5%, more preferably 20 to 90%, and better still 50 to 70% by weight with respect to its total weight, of the aqueous phase,
- b) 0.1 to 90%, preferably 0.5 to 85%, more preferably 10 to 80%, and better still 30 to 50% by weight with respect to its total weight, of the non-aqueous phase,
the sum of a)+b) being equal to 100%.

The inventive formulation is also preferably characterized in that it includes 0.05 to 10%, preferably 0.05 to 5%, more preferably 0.05 to 2%, and even better, 0.1% to 1% by dry weight with respect to its total weight, of said amphiphilic comb copolymer.

The inventive formulation is also preferably characterized in that its non-aqueous phase is composed of bodies that are non-miscible in water, liquid fats at room temperature (25° C.) and/or solid fats at room temperature such as waxes, pasty fats, gums and their mixtures. These fats can be of animal, vegetable, mineral or synthetic origin. In addition, the aqueous phase may contain lipophilic organic solvents.

The inventive formulation is also preferably characterized in that it can also contain in a particular phase, pigments and/or nacres and/or fillers commonly used in cosmetic compositions.

The inventive formulation is also preferably characterized in that it can also contain other colouring materials chosen from among the water-soluble dyes or fat-soluble dyes that are well known to the person skilled in the art.

The inventive formulation is also preferably characterized in that it can contain an additional polymer which is a film-forming polymer. According to this invention, a "film-forming polymer" means a polymer capable of forming alone or in the presence of a filmification auxiliary agent, a continuous and adherent film on a support, including on keratinic materials.

The inventive formulation is also preferably characterized in that it can contain at least one surface active or emulsifying agent.

Finally, The inventive formulation is also preferably characterized in that it can contain ingredients commonly used in cosmetics, such as vitamins, perfumes, nacrating agents, gelling agents, trace elements, softeners, retention aids, alkalinizing or acidifying agents, preservatives, solar filters, antioxidants, anti hair loss agents, anti-dandruff agents, propellant agents, ceramides, foaming agents, emollients, humectants, texture agents, brighteners, anti-aging agents, moisturizing agents, anti-stress and/or soothing agents, dermoprotective agents, or their mixtures.

Another object of the present invention is the use in a formulation, preferably a cosmetic formulation such as noted above, of at least one non-water soluble amphiphilic comb copolymer comprising, consisting essentially of, or consisting of, expressed in % by weight of each of the comonomers:

a) from 30% to 60% of at least one hydroxy and/or methoxy polyalkylene glycol monomer with the formula R-(EO)$_m$-(PO)$_n$-R', with:
  m and n designating integers that are less than or equal to 150, with at least one of them being a non-zero,
  EO and PO respectively designating ethylene oxide and propylene oxide,
  R designating the methacrylate or methacrylurethane function,
  R' designating a hydroxy or methoxy, group,
b) from 20% to 60% of at least one hydrophobic monomer chosen from styrene and paratertiobutylstyrene, and the (meth)acrylic esters with 1 to 4 carbon atoms on the ester group,
c) from 0.1% to 10% of at least one monomer which is acrylic and/or methacrylic acid,
d) from 0 to 15% of an associative monomer with the formula R-(EO)$_m$-(PO)$_n$-R', with:
  m and n designating integers that are less than or equal to 150, with at least one of them being a non-zero,
  EO and PO respectively designating ethylene oxide and propylene oxide,
  R designating a polymerizable function, preferentially the methacrylate or methacrylurethane function,
  R' designating an alkyl or aryl or alkylaryl group with 8 to 36 carbon atoms, linear or branched,
e) from 0 to 5% of a monomer with at least two ethylenic unsaturations,
the sum of the percentages a), b), c), d) and e) being equal to 100%,
preferably used as a thickening agent of the formulation.

This utilisation is also characterized in that said formulation preferably has a pH less than or equal to 7, preferentially between 5 and 6.5, very preferentially between 5.5 and 6.

Another object of the present invention is a thickening process for a formulation, preferably a cosmetic formulation, by the introduction to it of at least one non-water soluble amphiphilic comb copolymer comprising, consisting essentially of, or consisting of, expressed in % by weight of each of the comonomers:
a) from 30% to 60% of at least one hydroxy and/or methoxy polyalkylene glycol monomer with the formula R-(EO)$_m$-(PO)$_n$-R', with:
  m and n designating integers that are less than or equal to 150, with at least one of them being a non-zero,
  EO and PO respectively designating ethylene oxide and propylene oxide,
  R designating the methacrylate or methacrylurethane function,
  R' designating a hydroxy or methoxy, group,
b) from 20% to 60% of at least one hydrophobic monomer chosen from styrene and paratertiobutylstyrene, and the (meth)acrylic esters with 1 to 4 carbon atoms on the ester group,
c) from 0.1% to 10% of at least one monomer which is acrylic and/or methacrylic acid,
d) from 0 to 15% of an associative monomer with the formula R-(EO)$_m$-(PO)$_n$-R', with:
  m and n designating integers that are less than or equal to 150, with at least one of them being a non-zero,
  EO and PO respectively designating ethylene oxide and propylene oxide,
  R designating a polymerizable function, preferentially the methacrylate or methacrylurethane function,
  R' designating an alkyl or aryl or alkylaryl group with 8 to 36 carbon atoms, linear or branched,
e) from 0 to 5% of a monomer with at least two ethylenic unsaturations,
the sum of the percentages a), b), c), d) and e) being equal to 100%.

This process is also preferably characterized in that the pH of the said formulation is less than or equal to 7, more preferentially between 5 and 6.5, very preferentially between 5.5 and 6.

The following examples will allow a better understanding of the invention, without however limiting its scope.

EXAMPLES

Example 1

This example deals with the thickening at a pH value of 5.5 of a cosmetic composition which is a body nourishing cream.

It begins by the preparation of a formulation from the following 2 phases A and B.

Phase A:
DC345 (Dow™ Corning) (5.0 g)
DC200/100CS (Dow™ Corning) (4.0 g)
Emulium Delta (Gattefosse™) (3.0 g)
MOD (Gattefosse™) (3.0 g)
Labrafac CC (Gattefosse™) (3.0 g)
IPP (Brenntag™) (3.0 g)
Phenonip (Clariant™) (0.5 g)
Phase B:
water (QS 100 g)
Thickener to be tested Each phase is produced by the mixing of its different constituents under agitation.

Mixture A is then melted in a 150 ml beaker at 70° C. without overheating.

Mixture B is then heated to 70° C. The latter is emulsified in mixture A under agitation (using an Ultra-Turax device) for 2 minutes at 6,000 RPM. The pH of the formulation is adjusted to 5.5 using sodium hydroxide.

It is then left to cool to room temperature to obtain a formulation with a creamy appearance.

Table 1 gives the composition (in % by weight of each of the comonomers) of copolymers of according to the invention which have been tested.

TABLE 1

| Test No. | MAA | AA | Meth $C_{22}(EO)_{25}$ | Meth $C_{20}(EO)_{36}$ | Meth $c_{32}(EO)_{25}$ | PEM 3070 | MAMPEG 5000 | EA | p(tBu)Sty |
|---|---|---|---|---|---|---|---|---|---|
| 1 | 8 | 0 | 3.5 | 0 | 0 | 32 | 0 | 56.5 | 0 |
| 2 | 0 | 5.5 | 0 | 0 | 0 | 55 | 0 | 0 | 39.5 |
| 3 | 9 | 0 | 2.5 | 0 | 0 | 33.5 | 0 | 55 | 0 |
| 4 | 9 | 0 | 0 | 0 | 0 | 35 | 0 | 56 | 0 |
| 5 | 10 | 0 | 0 | 0 | 4 | 36 | 0 | 50 | 0 |
| 6 | 9.5 | 0 | 0 | 2.5 | 0 | 32 | 0 | 56 | 0 |
| 7 | 9.5 | 0 | 2.5 | 0 | 0 | 32 | 0 | 56 | 0 |

TABLE 1-continued

| Test No. | MAA | AA | Meth $C_{22}(EO)_{25}$ | Meth $C_{20}(EO)_{36}$ | Meth $C_{32}(EO)_{25}$ | PEM 3070 | MAMPEG 5000 | EA | p(tBu)Sty |
|---|---|---|---|---|---|---|---|---|---|
| 8 | 9.5 | 0 | 2.5 | 0 | 0 | 0 | 32 | 56 | 0 |
| 9 | 9 | 0 | 2 | 0 | 0 | 0 | 45 | 44 | 0 | with:

MAA: methacrylic acid

AA: acrylic acid

Meth $C_{22}(EO)_{25}$: monomer with the formula R-$(EO)_m$-$(PO)_n$-R', where R designates the methacrylate function, n=25, m=0 and R' is the linear alkyl group with 22 carbon atoms Meth $C_{20}(EO)_{36}$: monomer with the formula R-$(EO)_m$-$(PO)_n$-R', where R designates the methacrylate function, n=36, m=0 and R' is the linear alkyl group with 20 carbon atoms Meth $C_{32}(EO)_{25}$: monomer with the formula R-$(EO)_m$-$(PO)_n$-R', where R designates the methacrylate function, n=35, m=0 and R' is the linear alkyl group with 32 carbon atoms PEM3070: monomer with the formula R-$(EO)_m$-$(PO)_n$-R', where R designates the methacrylates function, n=30, m=70 and R' is the hydroxyl group MAMPEG5000: monomer with the formula R-$(EO)_m$-$(PO)_n$-R', where R designates the methacrylates function, n=114, m=0 and R' is the methoxy group EA: Ethyl Acrylate p(tBu)Sty: para-tert-butylstyrene PEM3070 is a monomer resulting from technology as described in U.S. Pat. No. 6,034,208.

MAMPEG5000 is marketed by the Coatex™ company under the name Norsocryl™ 405.

Each of the polymers according to tests No. 1 to 9 is introduced into the previous formulation at a rate of 0.7% by dry weight with respect to the total weight of the said formulation.

The Brookfield viscosity of the formulation at 25° C. and 20 RPM is then measured.

Test No. 10 is a reference test that does not use the thickener.

The results are listed in table 2.

TABLE 2

| Test No. | Viscosity (mPa · s) |
|---|---|
| 1 | 5,400 |
| 2 | 8,150 |
| 3 | 5,800 |
| 4 | 5,200 |
| 5 | 6,500 |
| 6 | 5,400 |
| 7 | 6,500 |
| 8 | 5,300 |
| 9 | 5,100 |
| 10 | 3,800 |

Without a thickener, the formulation according to test No. 10 is not stable.

It will be apparent for the rest that the polymer according to the invention enables effective thickening, that is to say to the same level as a marketed polymer, a cosmetic formulation at a pH equal to 5.5.

The above written description of the invention provides a manner and process of making and using it such that any person skilled in this art is enabled to make and use the same, this enablement being provided in particular for the subject matter of the appended claims, which make up a part of the original description.

As used herein, the words "a" and "an" and the like carry the meaning of "one or more." The phrases "selected from the group consisting of," "chosen from," and the like include mixtures of the specified materials. Terms such as "contain(s)" and the like are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A formulation comprising an aqueous phase, a non-aqueous phase, and an amphiphilic non-water-soluble comb copolymer, wherein the amphiphilic non-water-soluble comb copolymer, in % by weight of each of its comonomers, comprises:

a) from 30% to 60% of a hydroxy polyalkylene glycol monomer, a methoxy polyalkylene glycol monomer, or both, having formula R-$(EO)_m$-$(PO)_n$-R', wherein m and n are each independently an integer less than or equal to 150, with at least one of m or n being non-zero, EO and PO are respectively ethylene oxide and propylene oxide, R is a methacrylate or methacrylurethane function, and R' is a hydroxy or methoxy, group;

b) from 20% to 60% of at least one hydrophobic monomer selected from the group consisting of styrene, paratertiobutylstyrene, and (meth)acrylic ester comprising 1 to 4 carbon atoms on an ester group;

c) from 0.1% to 10% of a monomer which is acrylic acid, methacrylic acid, or both;

d) from 0 to 15% of an associative monomer having formula R-$(EO)_m$-$(PO)_n$-R', wherein m and n are each independently an integer less than or equal to 150, with at least one of m or n being non-zero, EO and PO are respectively ethylene oxide and propylene oxide, R is a methacrylate or methacrylurethane function, R' is an alkyl, aryl, or alkylaryl group comprising 8 to 36 carbon atoms, linear or branched; and e) from 0 to 5% of a monomer with at least two ethylenic unsaturations, wherein the percentages of a), b), c), d), and e) sum to 100%, and wherein the copolymer has a mean molar mass by weight of between 1,000,000 and 15,000,000 g/mol as determined by Gel Permeation Chromatography.

2. The formulation according to claim 1, wherein the copolymer has a mean molar mass by weight of between 1,000,000 and 6,000,000 g/mol as determined by Gel Permeation Chromatography.

3. The formulation according to claim 1, comprising:

50 to 70% by weight with respect to total weight of the aqueous phase, and 30 to 50% by weight with respect to total weight of the non-aqueous phase.

4. The formulation according to claim 1, comprising 0.05 to 10% by dry weight, relative to a total weight, of the amphiphilic comb copolymer.

5. The formulation according to claim 1, further comprising a water-soluble dye, a fat-soluble dye, or both.

6. The formulation according to claim 1, further comprising a surface active agent or an emulsifying agent.

7. The formulation according to claim 1, wherein the formulation is a cosmetic formulation having a pH of 5-7.

8. The formulation according to claim 7, further comprising a film-forming polymer.

9. The formulation according to claim 1, wherein the amphiphilic non-water-soluble comb copolymer comprises said associative monomer having the formula $R\text{-}(EO)_m\text{-}(PO)_n\text{-}R'$.

10. The formulation according to claim 1, wherein the amphiphilic non-water-soluble comb copolymer comprises said monomer with at least two ethylenic unsaturations.

11. The formulation according to claim 9, wherein the amphiphilic non-water-soluble comb copolymer comprises said monomer with at least two ethylenic unsaturations.

* * * * *